(12) United States Patent
Zhou et al.

(10) Patent No.: US 9,465,022 B2
(45) Date of Patent: Oct. 11, 2016

(54) METHOD FOR REAL-TIME ON-LINE MONITORING OF CONCRETE FREEZE-THAW DAMAGE

(71) Applicants: SHANDONG HI-SPEED QINGDAO HIGHWAY COMPANY LIMITED, Shandong (CN); TSINGHUA UNIVERSITY, Beijing (CN)

(72) Inventors: Yong Zhou, Shandong (CN); Xingying Lu, Beijing (CN); Xinpeng Shao, Shandong (CN); Hui Ji, Shandong (CN); Baolin Guo, Shandong (CN); Xiaoqian Wang, Shandong (CN)

(73) Assignees: TSINGHUA UNIVERSITY, Beijing (CN); SHANDONG HI-SPEED QINGDAO HIGHWAY COMPANY LIMITED, Shandong (CN)

( * ) Notice: Subject to any disclaimer, the term of this patent is extended or adjusted under 35 U.S.C. 154(b) by 197 days.

(21) Appl. No.: 14/234,918

(22) PCT Filed: Nov. 7, 2012

(86) PCT No.: PCT/CN2012/084198
§ 371 (c)(1),
(2) Date: Jan. 24, 2014

(87) PCT Pub. No.: WO2013/075584
PCT Pub. Date: May 30, 2013

(65) Prior Publication Data
US 2014/0245820 A1   Sep. 4, 2014

(30) Foreign Application Priority Data
Nov. 23, 2011 (CN) .......................... 2011 1 0375744

(51) Int. Cl.
*G01N 33/38* (2006.01)
*G01N 17/00* (2006.01)

(52) U.S. Cl.
CPC ............ *G01N 33/383* (2013.01); *G01N 17/00* (2013.01)

(58) Field of Classification Search
CPC ..................................... G01N 33/383
USPC ...................................... 73/86, 805
See application file for complete search history.

(56) References Cited

U.S. PATENT DOCUMENTS 7,922,808 B2 * 4/2011 Brower ................... C04B 28/02
                                                    106/713
8,739,634 B2 * 6/2014 Ong .......................... G01N 3/60
                                                    73/805

(Continued)

FOREIGN PATENT DOCUMENTS

| CN | 1438478 | 8/2003 |
| CN | 1837805 | 9/2006 |

(Continued)

OTHER PUBLICATIONS

Cai et al., Freeze-Thaw Durability of Concrete: Ice Formation Process, Cement and Conclete Research, vol. 28, No. 9.pp. 1281-1287, 1998.*

(Continued)

*Primary Examiner* — Hezron E Williams
*Assistant Examiner* — Hoang Nguyen
(74) *Attorney, Agent, or Firm* — Nixon & Vanderhye P.C.

(57) ABSTRACT

A method for real-time and in-situ monitoring of freeze-thaw damage to concrete, comprising embedding pairs of gradient electrical resistance probes into a surface of concrete being monitored at a depth of 0-50 mm, the paired gradient electrical resistance probes having an anti-corrosion metal bar, with the buried depth gradient of different pairs of electrical resistance probes being in the range of 1 mm to 20 mm, and the buried depth gradient of the pair of electrical resistance probes nearest to the surface being less than 5 mm; transmitting an impedance value of the concrete measured by the paired gradient electrical resistance probes to a monitoring center for processing; and evaluating a spalling status of freeze-thaw damage to the concrete based on changes in impedance value which may be abrupt. Real-time in-situ monitoring of the freeze-thaw damage of concrete can be achieved by the electrical resistance probes and monitoring center of this invention.

1 Claim, 2 Drawing Sheets

(56) References Cited

U.S. PATENT DOCUMENTS

| | | | | |
|---|---|---|---|---|
| 2005/0284340 | A1* | 12/2005 | Vickers | C04B 16/085 106/802 |
| 2006/0281836 | A1* | 12/2006 | Kerns | C04B 16/04 524/2 |
| 2014/0297204 | A1* | 10/2014 | Biesak | G01F 17/00 702/56 |

FOREIGN PATENT DOCUMENTS

| | | |
|---|---|---|
| CN | 101226187 | 7/2008 |
| CN | 102507661 | 6/2012 |
| DE | 3112183 | 10/1982 |
| WO | 96/30741 | 10/1996 |
| WO | 02/10715 | 2/2002 |

OTHER PUBLICATIONS

Perron et al., Freezing of water in portland cement paste—an ac impedance spectroscopy study, Science Direct, Cement and Concrete Composites, vol. 24, Issue 5, Oct. 2002, pp. 467-475.*

International Search Report for PCT/CN2012/084198, mailed Feb. 28, 2013.

Xu, X. et al., "Prediction of the life of concrete structures under the effects of freezing-thawing and other special environments", Proceedings of Scientific Forum of Durability and Design Methods of Concrete Structures in Coastal Regions and the 6$^{th}$ National Academic Seminar on Concrete Durability, (2004), pp. 75-83.

Li, M. et al., "Electrical Resistance Measurement to Assess Curing Efficiency of Concrete", Journal of Building Materials, vol. 14, No. 4, (Aug. 2011), pp. 473-477.

Yang, Z. et al., "Study of freezing and thawing test of concrete by AC impedance technique", Journal of Building Materials, vol. 2, No. 4, (Dec. 1999), pp. 365-368.

Pan, Z., "Use CFRC's Functional Performance to Monitoring the Damage in Concrete Structure", Chinese Master'S Theses, No. 3, (Mar. 15, 2006), pp. 31-38.

Liu, K. et al., "Durability monitoring of bridges", Corrosion and Protection, vol. 27, No. 4, (Apr. 2006), pp. 178-180.

Cai, H. et al., "Freeze-thaw durability of concrete: ice for formation process in pores", Cement and Concrete Research, vol. 28, No. 9, (1998), pp. 1281-1287.

Cao, J. et al., "Damage evolution during freeze-thaw cycling of cement mortar studied by electrical resistivity measurement", Cement and Concrete Research, vol. 32, (2002), pp. 1657-1661.

Raupach, M. et al., Long-term durability of hydrophobic treatment on concrete, Surface Coatings International Part B; Coatings Transactions, vol. 88, (May 2005), pp. 127-133.

* cited by examiner

US 9,465,022 B2

METHOD FOR REAL-TIME ON-LINE MONITORING OF CONCRETE FREEZE-THAW DAMAGE

This application is the U.S. national phase of International Application No. PCT/CN2012/084198, filed 7 Nov. 2012, which designated the U.S. and claims priority to CN Application No. 201110375744.8 filed 23 Nov. 2011, the entire contents of each of which are hereby incorporated by reference.

FIELD OF THIS INVENTION

This invention refers to the technical field of nondestructive monitoring of concrete, specifically a real-time and online monitoring method for freeze-thaw damage of concrete.

BACKGROUND TECHNOLOGY

With constantly changing climate, freezing of seawater alongside Bohai Bay not only threatens the trips of fishing boats, but also results in serious freeze-thaw damage to concrete structure along the beach and at sea. In the cold area of northern China, in order to ensure traffic safety, deicing salt is used to melt snow in winter; the thermal shock of deicing salt leads to the freeze-thaw damage on the concrete bridge surface or the road surface. The typical characteristic of freeze-thaw damage of concrete is the spalling of surface concrete. Obviously, the surface spalling of land concrete can be observed by unaided eyes, while the structure concrete at the bottom of offshore engineering is just the opposite, which goes against the timely maintenance of structure due to the difficulty of observation.

So far, no method for real time on-line monitoring of concrete freeze-thaw damage is disclosed.

THE CONTENT OF INVENTION

In order to overcome the shortcomings of prior art listed above; this invention provides a method for real-time and online monitoring freeze-thaw damage of concrete, which could monitor the freezing and thawing damages of the concrete real-time and online.

To achieve the mentioned goals, the technical scheme of the invention is as follow:

Method for real-time and online monitoring the freeze-thaw damage of concrete consists of the following steps:

Step One, embed pairs of gradient electrical resistance probes into surface of the monitoring concrete at the depth of 0-50 mm, the paired gradient electrical resistance probes comprise an anti-corrosion metal bar, and the buried depth gradient of different electrical resistance probes is in the range of 1 mm to 20 mm, and the buried depth of the pair of electrical resistance probes nearest to the surface is less than 5 mm.

Step Two, transmit the impedance value of the concrete measured by the paired gradient electrical resistance probes to the monitor center for processing;

Step Three, fudge the spalling status of freeze-thaw damage of concrete through the abrupt change in impedance value A. The electrical resistance probes with the same depth meet with abrupt changes for the concrete impedance value and there are three status:

a. On the curve of Impedance-Time, the impedance value changes from relatively stable to infinite, at the moment the concrete suffers spalling and there is no free water seeped into the concrete;

b. On the curve of Impedance-Time, the impedance value changes from relatively stable to almost zero, at the moment the concrete suffers spalling and free water seeped into the concrete;

c. On the curve of Impedance-Time, the impedance value presents a vertical change in trend, if the impedance value rises, the concrete suffers spalling and there is no free water seeped into the concrete, if the impedance value decreases, it suffers spalling and free water seeped into the concrete.

B. From the surface to the interior, as for the buried electrical resistance probe of one layer or deeper, if the impedance value of the concrete meets with the status as mentioned in A, refer to A and judge according to the standards.

Real-time online monitoring of the freeze-thaw damage of concrete can be achieved by the electrical resistance probes and monitoring center of this invention.

EMBODIMENTS

Detailed description of the invention with reference to the attached Figures and examples as follows.

Figure 1:
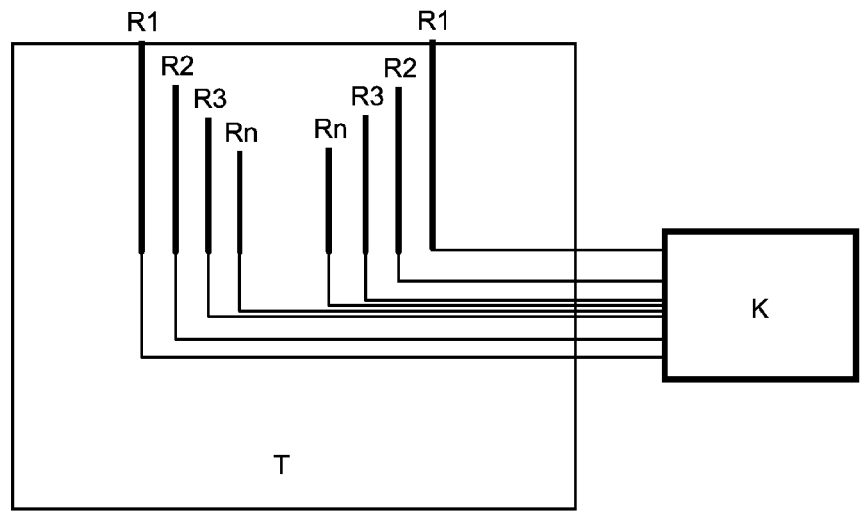
FIG. 1 is the principle diagram of monitoring freeze-thaw damage of concrete in the invention.
Figure 2:
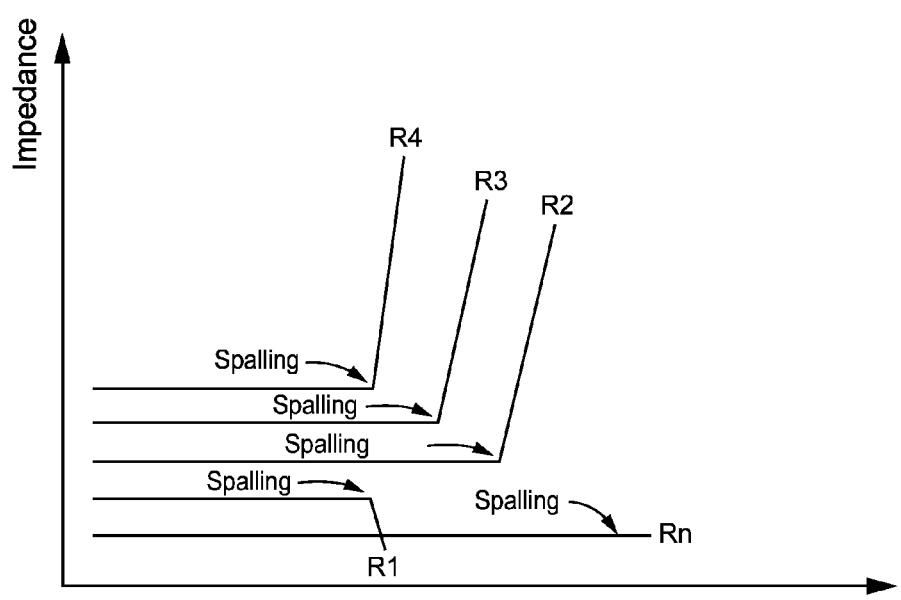
FIG. 2 is the schematic diagram of changes in the impedance value of the concrete surface with the time.

According to FIG. 1, method for real-time and online monitoring freeze-thaw damage of concrete contains the following steps:

Step One, referring to FIG. 1 and FIG. 2, embed pairs of gradient electrical resistance probes R1-Rn into concrete T at the depth of 0-50 mm from a surface of the concrete, electrical resistance probes R1-Rn are connected to the impedance meter K, the paired gradient electrical resistance probes comprise an anti-corrosion metal bar, and the buried depth gradient of different electrical resistance probes is in the range of 1 mm to 20 mm, the buried depth gradient of the electrical resistance probes close to the surface shall be less than 5 mm, so as to identify the freeze-thaw damage to the concrete at an early stage of damage in the outermost surface.

Step Two, transmit the concrete impedance value tested by paired gradient electrical resistance probes to the monitoring center for processing.

Step Three, judge the condition of freeze-thaw spalling of concrete by the abrupt changes in concrete impedance value. There are two judging standards according to the conditions:

A. The electrical resistance probes with the same depth meet with abrupt changes for the concrete impedance value and there are three status: Refer to FIG. 2, a. On the curve of Impedance-Time, the impedance value changes from relative stable to infinite, at the moment the concrete suffers spalling and there is no free water seeped into the concrete;

b. On the curve of Impedance-Time, the impedance value changes from relative stable to almost zero, at the moment the concrete suffers spalling and there is free water seeped into the concrete;

c. On the curve of Impedance-Time, the impedance value shows a vertical change in trend, if the value rises, the concrete suffers spalling with no free water immerses, while if the value decreases, it suffers spalling and free water seeped into the concrete.

B. From the exterior to the interior, as for the buried electrical resistance probe of one layer or deeper, if the impedance value of the concrete meets with the status as mentioned in A, refer to A and make conclusions according to the standards.

The technical principle of the method is that the electrical resistance probe shows open circuit, short circuit that leads to the dramatic changes in concrete impedance value when the concrete surface is spalling, thereby showing the freeze-thaw damage of the concrete; As for the regions that not suffer from freezing damage, the impedance value of concrete remains relatively stable, without any significant changes altogether.

EXAMPLES

Method for real-time and online monitoring freeze-thaw damage of concrete contains the following steps:

Step One, in the test specimen of concrete with coating in the tidal range zone, embed 6 pairs of gradient electrical resistance probes into surface of the concrete monitoring at the depth of 0~50 mm, the paired gradient electrical resistance probe is brass(H60) with the diameter of 6 mm, the electrode distances of which are all 100 mm. The electrical resistance probe from the exterior to the interior is sequenced from No. 1 to No. 6, and the buried depths are respectively 0, 5, 10, 15, 20 and 40 mm.

Step Two, transmit the concrete impedance value tested by paired gradient electrical resistance probe to the monitoring center for processing.

Figure 3:
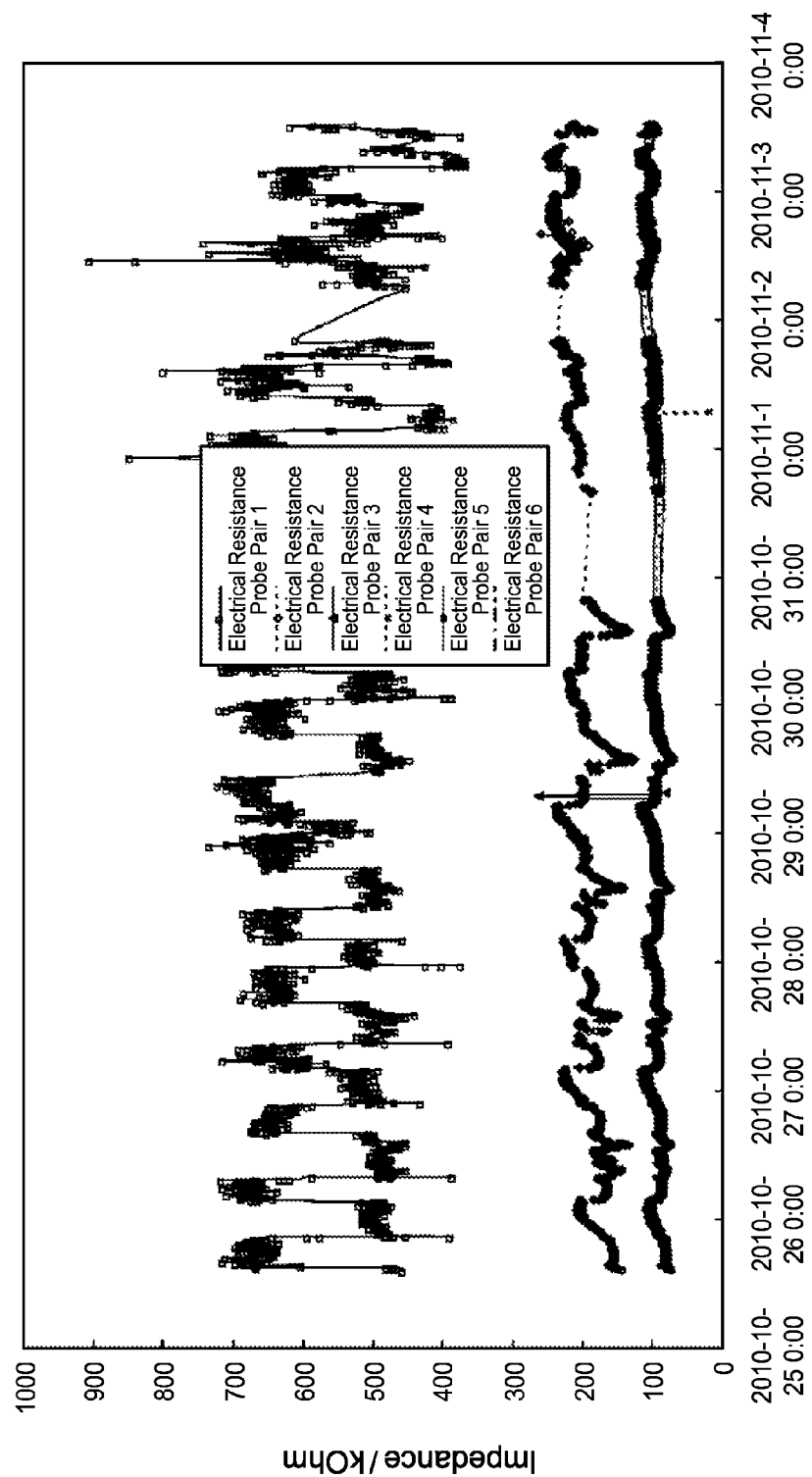
FIG. 3 is the diagram of the changes in impedance value of the concrete with time when embedding the electrical resistance probe in different depth.

Step Three, judge the condition of freeze-thaw spalling of concrete by the abrupt changes in concrete impedance value; according to FIG. 3, the concrete impedance at the depth of 5 mm from the coating is strongly affected by the external environment while at the depth of 10-40 mm it is essentially unchanged. In addition, because of the coating on the concrete test specimen surface, the impedance value of electrical resistance probe in the first layer varies in the range of 500 to 700 kOhm. When it suddenly decreases to dozens of ohm, the coating is broken off. When the value changes from dozens of ohm to infinite during receding tide while decreases to almost zero during rising tide, it can be concluded that the surface concrete suffers spalling; By that analogy, when concrete resistance between the electrical resistance probes from layer 2 to layer 6 changes dramatically, on condition that the corresponding concrete impedance value changes from dozens of ohm to infinite during receding tide and to almost zero during rising tide, it can be proved that the concrete suffers spalling at that depth.

The invention claimed is:

1. A method for real-time and in-situ monitoring the freeze-thaw damage of concrete, including the following steps:
   (1)—embed pairs of gradient electrical resistance probes into a surface of the concrete at the depth of 0~50 mm, each of the pairs of gradient electrical resistance probes comprising an anti-corrosion metal bar, the buried depth gradient between different pairs of electrical resistance probes being in the range of 1 mm to 20 mm, and the buried depth gradient of the pair of electrical resistance probes nearest to the surface being less than 5 mm;
   (2)—transmit the impedance value of the concrete measured by each of the pairs of gradient electrical resistance probes to a monitor center for processing;
   (3)—evaluate a spalling status of freeze-thaw damage to the concrete based on changes in impedance value as reflected in a curve of impedance versus time, there being two evaluation standards according to conditions:
   (A). The electrical resistance probes with a same depth meet with abrupt changes for the concrete impedance value and there are three statuses:
      i. on the curve of Impedance-Time, an impedance value changes from relatively stable to infinite at the moment the concrete suffers spalling and free water does not penetrate the concrete;
      ii. on the curve of Impedance-Time, the impedance value changes from relatively stable to almost zero at the moment the concrete suffers spalling and free water penetrates into the concrete;
      iii. on the curve of Impedance-Time, where the impedance value presents a vertical change in trend: if the impedance value rises, the concrete suffers spalling and free water does not penetrate the concrete, whereas if the impedance value decreases, it suffers spalling and free water penetrates into the concrete; and
   (B). From the surface to the interior, for each pair of buried electrical resistance probes at each layer, if the impedance value of the concrete meets with the status as mentioned in A, refer to A and judge according to the standards discussed in A.

* * * * *

UNITED STATES PATENT AND TRADEMARK OFFICE
CERTIFICATE OF CORRECTION

PATENT NO.       : 9,465,022 B2                                                         Page 1 of 1
APPLICATION NO.  : 14/234918
DATED            : October 11, 2016
INVENTOR(S)      : Zhou et al.

It is certified that error appears in the above-identified patent and that said Letters Patent is hereby corrected as shown below:

Title Page, Item 72, The second inventor is listed as Xingying Lu should read Xinying Lu.

Signed and Sealed this
Sixth Day of December, 2016

Michelle K. Lee
*Director of the United States Patent and Trademark Office*